US012703011B2

(12) United States Patent
Heymann et al.

(10) Patent No.: US 12,703,011 B2
(45) Date of Patent: Aug. 11, 2026

(54) AUTOMATIC EMITTER POINT CLEANERS WITH A DETECTION SURFACE CLEANER

(71) Applicant: ILLINOIS TOOL WORKS INC., Glenview, IL (US)

(72) Inventors: Steven Bernard Heymann, Los Gatos, CA (US); Aleksey Klochkov, San Francisco, CA (US); Juan Guerrero, Berkeley, CA (US); Edward Anthony Oldynski, Martinez, CA (US)

(73) Assignee: Illinois Tool Works Inc., Glenview, IL (US)

( * ) Notice: Subject to any disclaimer, the term of this patent is extended or adjusted under 35 U.S.C. 154(b) by 239 days.

(21) Appl. No.: 18/602,640

(22) Filed: Mar. 12, 2024

(65) Prior Publication Data

US 2024/0307926 A1 Sep. 19, 2024

Related U.S. Application Data

(60) Provisional application No. 63/489,831, filed on Mar. 13, 2023.

(51) Int. Cl.
*B08B 1/12* (2024.01)
*A46B 13/02* (2006.01)
(Continued)

(52) U.S. Cl.
CPC ................ *B08B 1/12* (2024.01); *A46B 13/02* (2013.01); *A61L 2/14* (2013.01); *A61L 2/26* (2013.01);
(Continued)

(58) Field of Classification Search
CPC .. B08B 1/12; B08B 1/143; B08B 1/20; B08B 1/30; B08B 6/00; A46B 13/02;
(Continued)

(56) References Cited

U.S. PATENT DOCUMENTS 5,493,383 A * 2/1996 Pozniakas .......... G03G 15/0105 15/256.5
5,768,087 A 6/1998 Vernitskiy
(Continued)

FOREIGN PATENT DOCUMENTS

CN 105849993 A 8/2016
KR 20150072063 6/2015
(Continued)

OTHER PUBLICATIONS

Int'l Search Report and Written Opinion Appln No. PCT/US2024/019652 mailed Jun. 11, 2024.
(Continued)

*Primary Examiner* — Sreeya Sreevatsa
(74) *Attorney, Agent, or Firm* — McAndrews, Held & Malloy, Ltd.

(57) ABSTRACT

Example automatic emitter point cleaning systems include: an emitter point configured to produce at least one of positive ions or negative ions within or proximate to an ionization delivery path; an emitter frame configured to hold the emitter point in or proximate to the ionization delivery path; a brush; a motor coupled to the brush to actuate the brush to move past the emitter point; a detection surface coupled to the brush; a sensor configured to detect when the brush is in a predetermined position with respect to a reference position by detecting the detection surface; and a detection surface cleaner configured to clean the detection surface while the brush moves with respect to the emitter frame.

20 Claims, 8 Drawing Sheets

(51) Int. Cl.

*A61L 2/14* (2006.01)
*A61L 2/26* (2006.01)
*B08B 1/14* (2024.01)
*B08B 1/20* (2024.01)
*B08B 1/30* (2024.01)

(52) U.S. Cl.

CPC ................ *B08B 1/143* (2024.01); *B08B 1/20* (2024.01); *B08B 1/30* (2024.01); *A46B 2200/3073* (2013.01); *A61L 2202/11* (2013.01); *A61L 2202/14* (2013.01); *A61L 2202/17* (2013.01)

(58) Field of Classification Search

CPC ..... A46B 2200/3073; A61L 2/14; A61L 2/26; A61L 2202/11; A61L 2202/14; A61L 2202/17

USPC .......................................................... 361/230

See application file for complete search history.

(56) References Cited

U.S. PATENT DOCUMENTS 12,070,781 B2 * 8/2024 Heymann ................. H05F 3/04
2010/0188793 A1 7/2010 Uchida
2015/0336109 A1 * 11/2015 Gefter ....................... B03C 3/41 95/2
2018/0272384 A1 * 9/2018 Heymann ............... H01T 19/04

FOREIGN PATENT DOCUMENTS

KR 20150072063 A * 6/2015 ............... H05F 3/04
TW 201210707 3/2012

OTHER PUBLICATIONS

Int'l Search Report and Written Opinion Appln No. PCT/US2018/023920 (14 pgs).
Taiwanese Search Report AppIn No. 111117615 dated Nov. 7, 2022.
Korean Office Action AppIn No. 10-2019-7031357 dated Jan. 9, 2023.

* cited by examiner

AUTOMATIC EMITTER POINT CLEANERS WITH A DETECTION SURFACE CLEANER

RELATED APPLICATIONS

The present application claims the benefit of U.S. Provisional Patent Application Ser. No. 63/489,831, filed Mar. 13, 2023, entitled "Automatic Emitter Point Cleaners with a Detection Surface Cleaner." The entirety of U.S. Provisional Patent Application Ser. No. 63/489,831 is expressly incorporated herein by reference.

FIELD OF THE DISCLOSURE

This disclosure relates generally to ionizers and, more particularly, to automatic emitter point cleaners with detection surface cleaner.

BACKGROUND

Ionizing devices that function as static eliminators or neutralizers may produce both polarities of ions that combine with and neutralize oppositely charged surfaces. Such devices are useful for maintaining electrostatically neutral conditions usually associated with the manufacture of electronic devices, especially semiconductors. Because these ionizers use discharge electrodes that produce an electric field, they tend to accumulate foreign particles at their emitter points or edges. This particle accumulation can cause an excess emission of ions of one polarity or the other, i.e., ion imbalance, whereby the area at which both polarities of ions are directed tends to become charged rather than electrostatically neutral.

SUMMARY

Automatic emitter point cleaners with a detection surface cleaner are disclosed, substantially as illustrated by and described in connection with at least one of the figures, as set forth more completely in the claims.

BRIEF DESCRIPTION OF THE DRAWINGS

The figures are not necessarily to scale. Where appropriate, similar or identical reference numbers are used to refer to similar or identical components.

DETAILED DESCRIPTION

Figure 1:
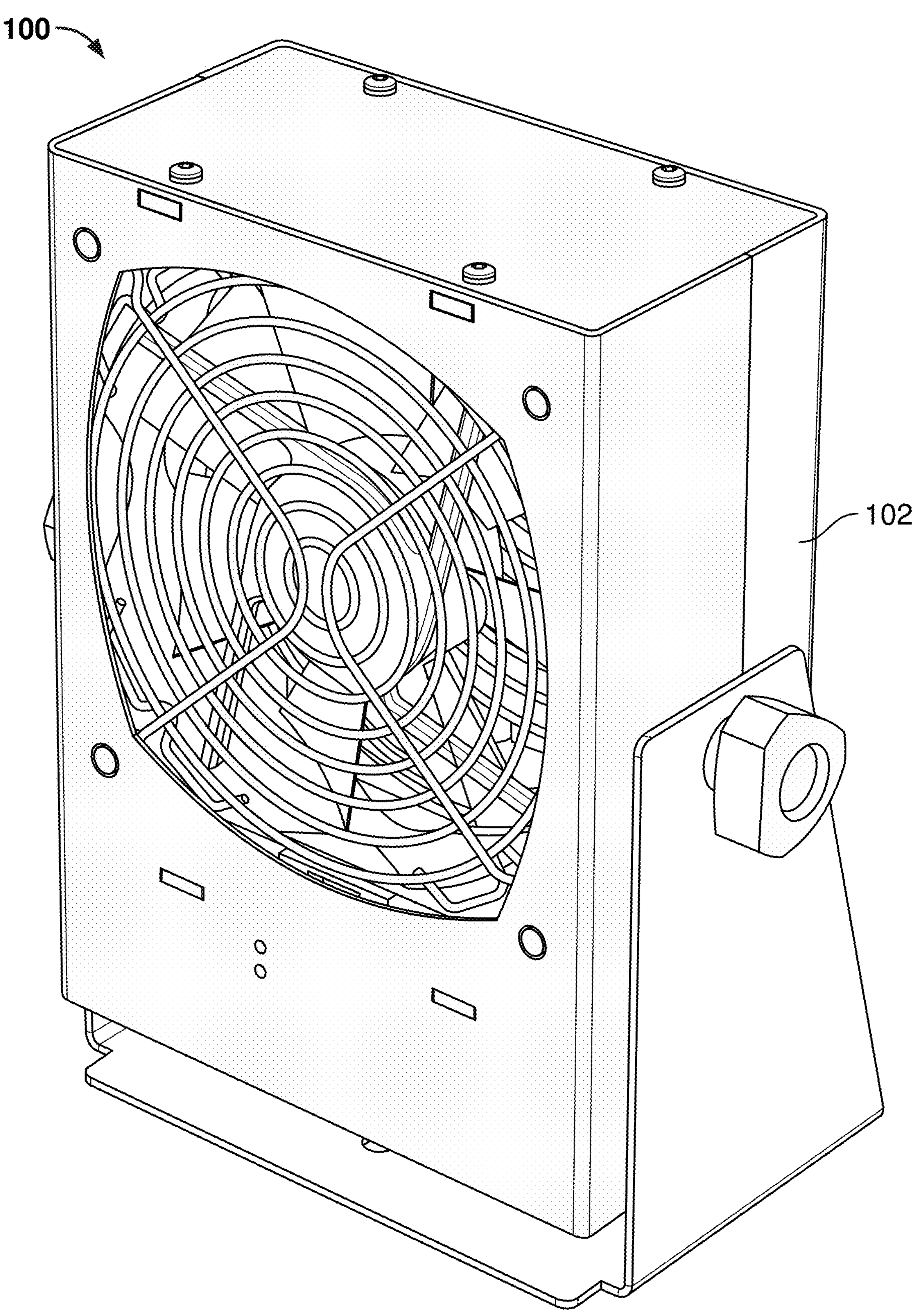
FIG. 1 is a view of an example DC corona ionizer, in accordance with aspects of this disclosure.

Conventional emitter point cleaning devices for ionizing blowers are connected to an axis of rotation of a fan, and the fan speed must be reduced from the speed during operation to enable emitter cleaning. As a result, conventional emitter point cleaning devices require a reduction in performance, or even disabling, of the ionizing blower to perform cleaning of the emitter points. A reduction in performance or disabling of the ionizing blower may provide a window in which charge buildup is more likely to damage sensitive devices.

Disclosed example systems enable emitter point cleaning for ionizing devices such that the ionizing device can continue to function (e.g., clean the air, neutralize charge, etc.) during cleaning. Disclosed example systems include a brush, a first ring coupled to the brush, a second ring to engage the first ring, and a motor to actuate the second ring such that the second ring actuates the first ring.

In some examples, the operation and actuation of the emitter point cleaner is controlled at least in part using a position sensor to determine the location of the emitter point cleaner. For example, the emitter point cleaner may be assigned a predetermined reference (or home) position, and detection of the emitter point cleaner (or detection surface coupled to the emitter point cleaner) at the reference position signifies that a cleaning procedure is complete. In some cases, a detection surface, used for detecting the position of the emitter point cleaner, can become contaminated, dirty, or otherwise more difficult to detect using the position sensor. Failure to detect the detection surface may result in performing excess cleaning cycles and/or excess wear on the emitter points and/or the emitter point cleaner.

Disclosed example automatic emitter point cleaning systems include: an emitter point configured to produce at least one of positive ions or negative ions within or proximate to an ionization delivery path; an emitter frame configured to hold the emitter point in or proximate to the ionization delivery path; a brush; a motor coupled to the brush to actuate the brush to move past the emitter point; a detection surface coupled to the brush; a sensor configured to detect when the brush is in a predetermined position with respect to a reference position by detecting the detection surface; and a detection surface cleaner configured to clean the detection surface while the brush moves with respect to the emitter frame.

Some example automatic emitter point cleaning systems further include a controller configured to control the motor to actuate the brush to move the brush past the emitter point. In some example automatic emitter point cleaning systems, the controller is configured to control the motor to actuate the brush based on at least one of a determination by the controller or an external signal. In some example automatic emitter point cleaning systems, the controller is configured to control the motor to stop the brush in response to the sensor detecting that the brush is in the predetermined position.

Some example automatic emitter point cleaning systems further include a plurality of emitter points in a same axial plane as the emitter point and the brush, in which the emitter frame is configured to hold the plurality of emitter points radially inward from the emitter frame and into the ionization path, and the motor is configured to move the brush into contact with each of the plurality of emitter points. In some example automatic emitter point cleaning systems, the plurality of emitter points are arranged in a substantially circular or polygonal arrangement. Some example automatic emitter point cleaning systems further include: a first gear coupled to the brush, configured to hold the brush in a same axial plane as the emitter point, and configured to move the brush into contact with the emitter point; and a second gear coupled between the motor and the first gear to actuate the first gear in response to actuation by the motor, in which the plurality of emitter points are arranged around or adjacent to an inner circumference of the first gear. In some example automatic emitter point cleaning systems, the substantially circular or polygonal arrangement is substantially coaxial with the fan.

In some example automatic emitter point cleaning systems, the motor is a bidirectional motor configured to move the brush in either direction. In some example automatic emitter point cleaning systems, the detection surface cleaner is positioned on the emitter frame adjacent the predetermined position. In some example automatic emitter point cleaning systems, the detection surface cleaner includes a pad configured to wipe contaminants from the detection surface as the detection surface moves over the pad. In some example automatic emitter point cleaning systems, the pad is a non-abrasive material.

In some example automatic emitter point cleaning systems, the detection surface cleaner is positioned on the emitter frame along a path of the detection surface. In some example automatic emitter point cleaning systems, the emitter point is configured to generate ionization. Some example automatic emitter point cleaning systems further include a first gear coupled to the brush, configured to hold the brush in a same axial plane as the emitter point, and configured to move the brush into contact with the emitter point; and a second gear coupled between the motor and the first gear to actuate the first gear in response to actuation by the motor.

In some example automatic emitter point cleaning systems, the detection surface includes a smooth, electrostatically non-conductive surface configured to resist adhesion by contaminants. In some example automatic emitter point cleaning systems, the detection surface is a polished surface. In some example automatic emitter point cleaning systems, the detection surface includes a coating configured to resist adhesion by contaminants. Some example automatic emitter point cleaning systems further include a fan configured to direct a stream of gas along the ionization path. In some example automatic emitter point cleaning systems, the emitter point is oriented in a same direction as the ionization path.

FIG. 1 is a view of an example DC corona ionizer 100. The ionizer 100 includes a housing 102 that holds a fan configured to blow a stream of air through an air path. As described in more detail below, the ionizer 100 includes ion emitters that emit positive and/or negative ions, and the fan blows the stream of air over the ion emitters, which results in a neutralization of electric charge that may be present in the air stream.

While examples disclosed below are described with reference to a DC corona ionizer, aspects of this disclosure may additionally or alternatively be used with an AC corona ionizer and/or a combination AC/DC corona ionizer.

Figure 2:
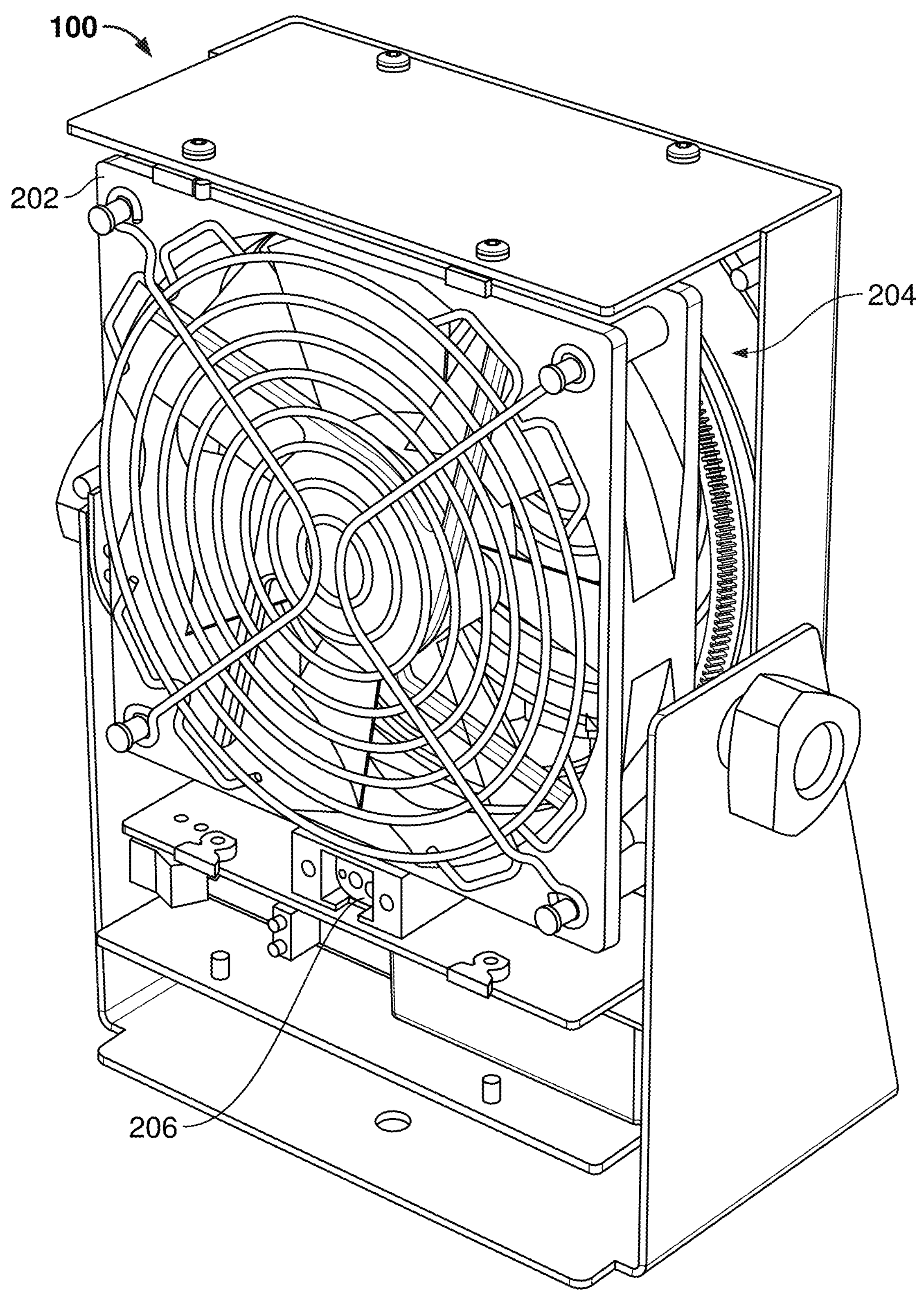
FIG. 2 is a view of an interior of the example DC corona ionizer of FIG. 1.

FIG. 2 is a view of an interior of the example DC corona ionizer 100 of FIG. 1. FIG. 2 illustrates the example fan 202 and an automatic emitter point cleaner 204. The automatic emitter point cleaner 204 includes a unidirectional or bidirectional DC motor 206. The DC motor 206 may receive a drive signal and/or DC current to actuate the automatic emitter point cleaner 204. The example fan 202 includes a housing 208 that may be used to mount the fan 202 to the housing 102 and/or to attach the automatic emitter point cleaner 204 to the fan 202.

The example DC motor 206 may be a brushless DC motor or any other type of AC or DC motor.

Figure 3:
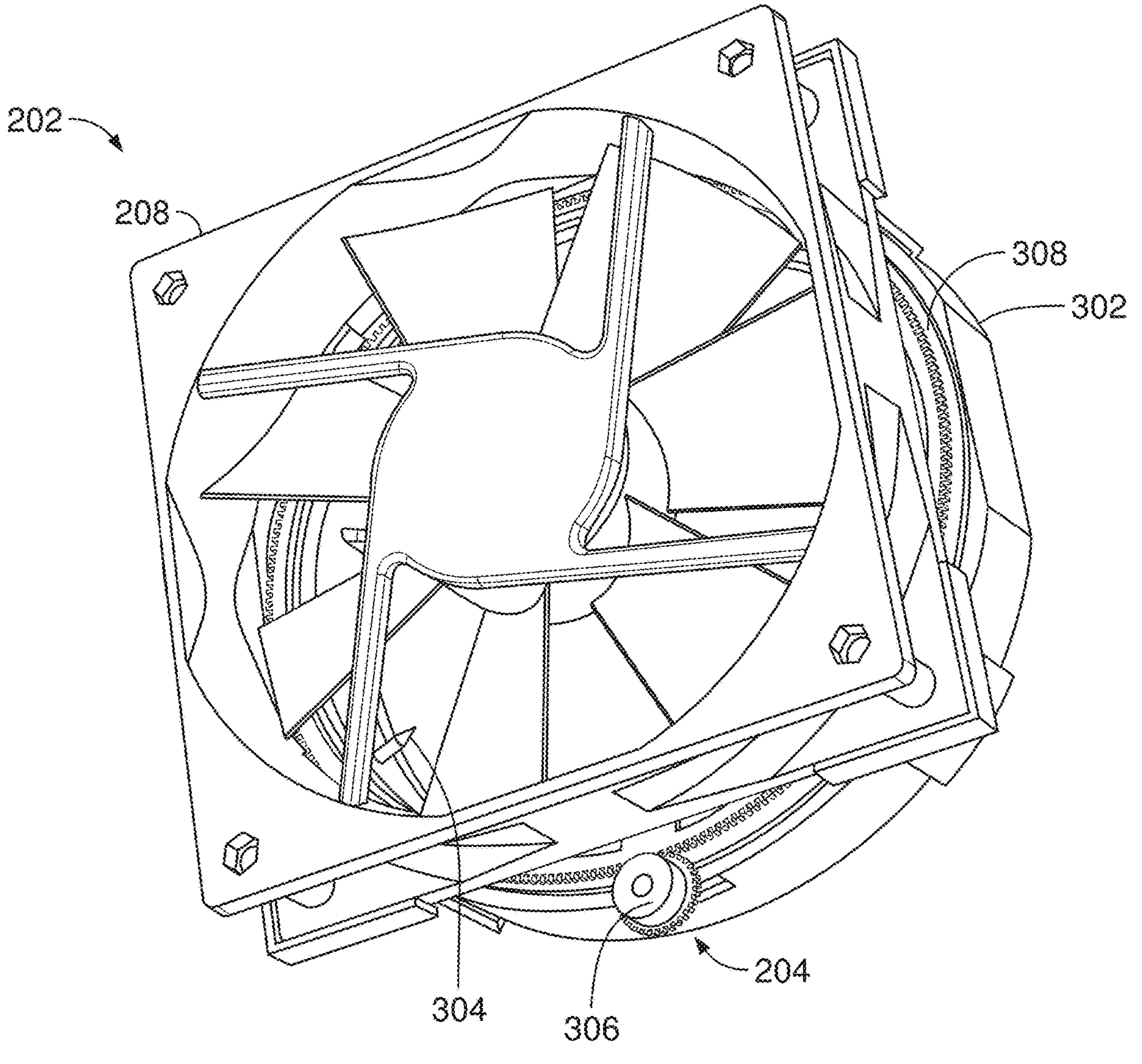
FIG. 3 is a view of the example fan of the DC corona ionizer attached to an automatic emitter point cleaner, in accordance with aspects of this disclosure.

FIG. 3 is a view of the example fan 202 of the DC corona ionizer 100 attached to automatic emitter point cleaner 204. The example ionizer 100 includes an emitter frame 302 that holds ion emitters 304 (also referred to as emitter points) in place around an inner circumference of the emitter frame 302, within the air path of the fan 202.

The example automatic emitter point cleaner 204 includes a pinion gear 306 and a spur gear 308. The spur gear 308 holds an emitter point brush. The pinion gear 306 is driven by the DC motor 206 of FIG. 2, and interfaces with the spur gear 308 to drive the spur gear 308. The example spur gear 308 and the emitter frame 302 are attached to the housing 208 of the fan 202 such that the spur gear 308 is substantially coaxial with the fan and holds the emitter point brush in a same plane as the ion emitters 304. The example ion emitters 304 are arranged in a substantially circular or polygonal arrangement around an inside of the spur gear 308 (e.g., substantially coaxial with the fan 202). The arrangement of the ion emitters 304 in FIG. 3 generate ionization into an ionization path 310 which is entrained by a stream of gas generated by the fan 202 and flowing along the ionization path 310.

Figure 4:
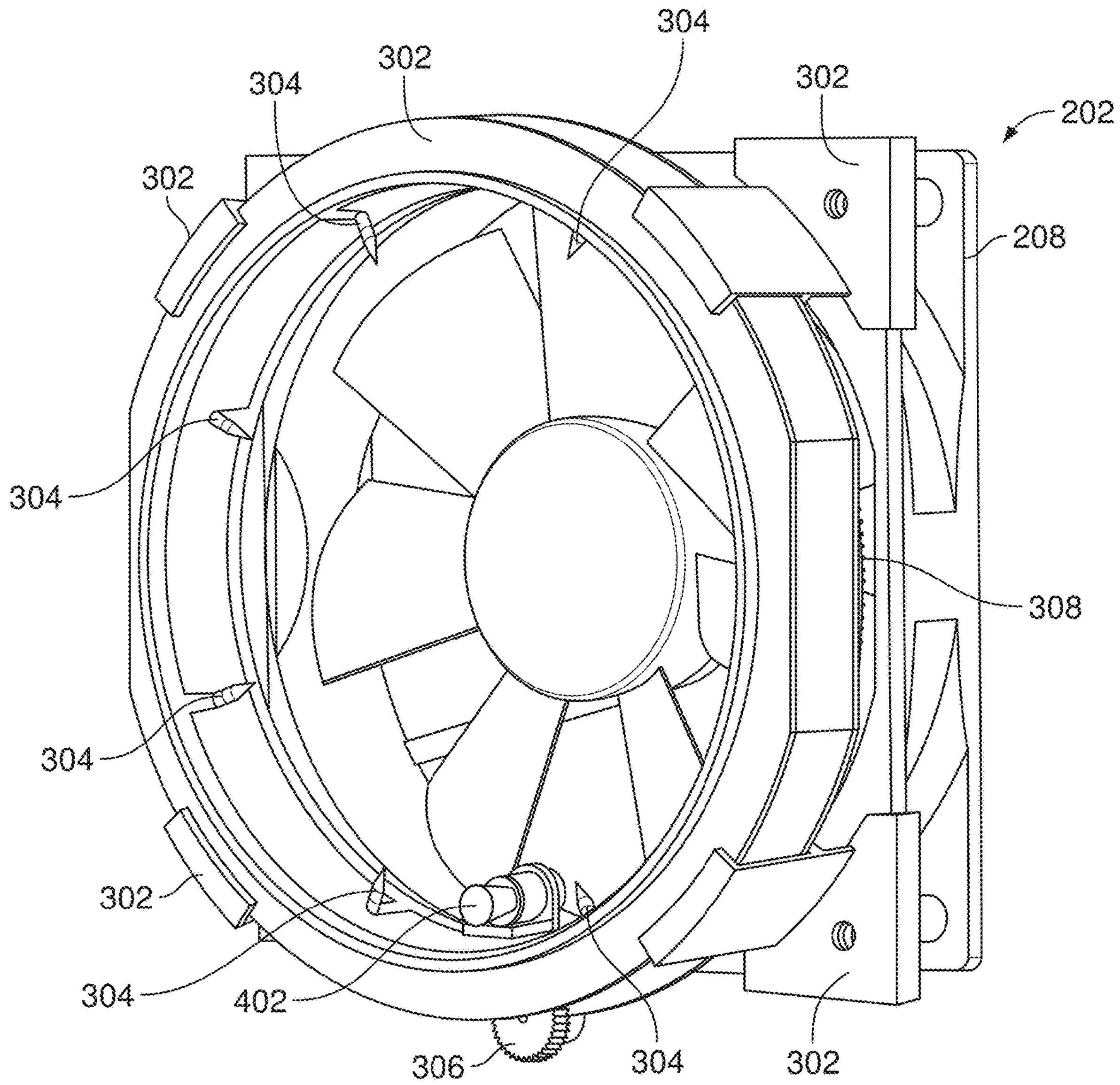
FIG. 4 is another view of the example fan and the automatic emitter point cleaner of FIG. 3.

FIG. 4 is another view of the example fan 202 and the automatic emitter point cleaner 204 of FIG. 3. FIG. 4 shows the fan 202, the housing 208, the example emitter frame 302, the emitters 304, the pinion gear 306, and the spur gear 308. An emitter point brush 402 is visible in FIG. 4. The emitter point brush 402 is in at least the same axial plane as the emitter points 304.

Figure 5:
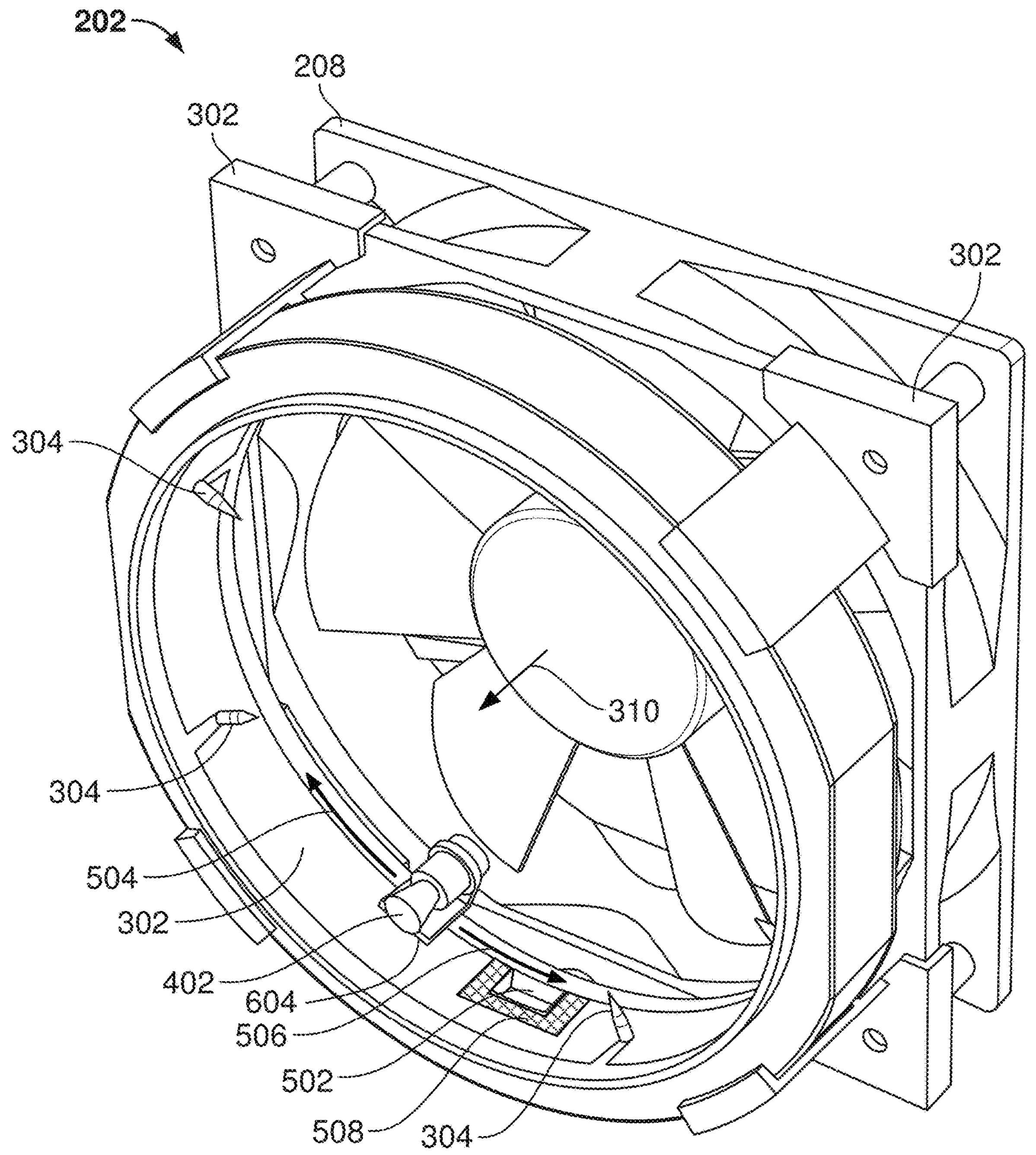
FIG. 5 is another view of the example fan and the automatic emitter point cleaner of FIG. 3.

FIG. 5 is another view of the example fan 202 and the automatic emitter point cleaner 204 of FIG. 3. In the view of FIG. 4, the emitter point brush 402 is shown in a known default, or home, position. The automatic emitter point cleaner 204 may include a position detector to identify (e.g., generate a signal) when the emitter point brush 402 is in the default position.

The example emitter frame 302 includes a detection window 502, through which a visual-type position detector (e.g., a laser detector) may identify when the emitter point brush 402 is proximate the detection window 502. Other position detectors include, for example, Hall effect sensors, switches, and/or any other type of proximity sensor and/or circuitry.

As illustrated in FIGS. 4 and 5, the spur gear 308 and the brush 402 may make complete and/or partial rotations around the inner circumference of the emitter frame 302 in one or both directions 504, 506. For example, the motor 206 of FIG. 2 drives the pinion gear 306 in one or both directions, which in turn causes rotation of the spur gear 308 and movement of the brush 402 around the inner circumference of the emitter frame 302. The example ionizer 100 may continue to run the fan 202 and generate ions via the emitters 304 while the brush 402 moves and cleans the emitters 304.

Figure 6:
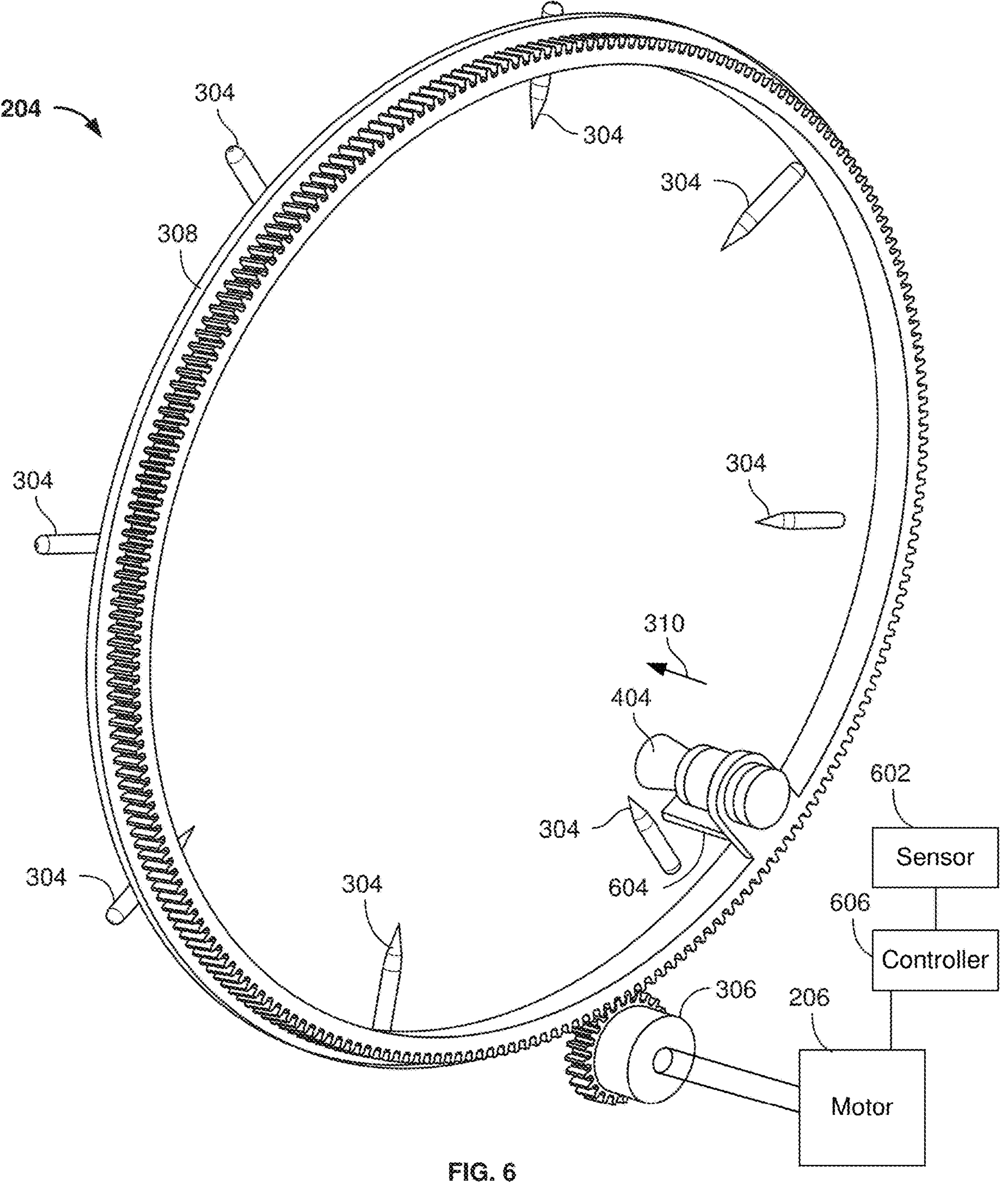
FIG. 6 is a view of example implementation of the automatic emitter point cleaner of FIGS. 3-5.

FIG. 6 is a view of example implementation of the automatic emitter point cleaner 204 of FIGS. 3-5. The structure of the example pinion gear 306, the example spur gear 308, and the example emitter point brush 402 are illustrated in FIG. 6.

The example automatic emitter point cleaner 204 of FIGS. 2-6 is motor driven (i.e., not centrifugal as in conventional systems). As a result, the automatic emitter point cleaner 204 may be activated to perform cleaning independently of the fan 202. For example, the automatic emitter point cleaner 204 may be activated with an internal timer (e.g., in a microprocessor controlling the fan 202 and/or emission of ions from the emitters 304) and/or from an external signal via an I/O connector.

Figure 7:
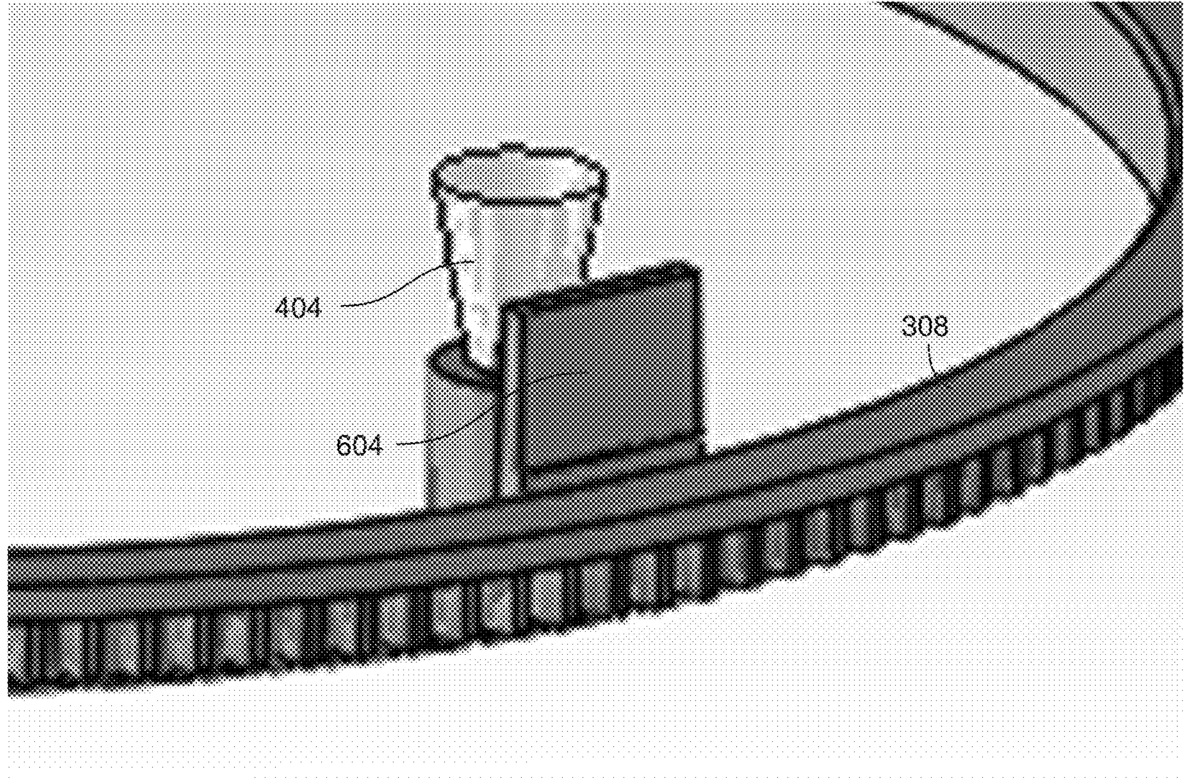
FIG. 7 is a perspective view of an example brush and detection surface that may be used to implement the automatic emitter point cleaner of FIGS. 3-5.

As the brush 404 is driven around the circumference of the emitter frame 302 during a cleaning process, a position sensor 602 is configured to detect when the brush 404 reaches a predetermined position. To improve the detection of the position of the brush 404, a detection surface 604 is coupled to the brush 404. In the example of FIGS. 5 and 6, the detection surface 604 is an outward facing surface (e.g., away from the center of the emitter frame 302 with respect to the brush 404), which aligns with the detection window 502. FIG. 7 is a perspective view of the example brush 404 and the example detection surface 604 that may be used to implement the automatic emitter point cleaner 204 of FIGS. 3-6. The position sensor 602 is likewise aligned with the detection window 502. When the detection surface 604 is located adjacent the detection window 502, the position sensor 602 detects the detection surface 604.

A controller 606 controls a motor 608 to actuate the brush 404, such as via a gearing system including the gears 306, 308. The controller 606 may actuate the brush 404 in response to, for example, the elapsing of a cleaning cycle time and/or in response to an external cleaning signal received at the controller 606. In response to the position sensor 602 detecting that the brush 404 is in the predetermined position (e.g., based on detecting the detection surface 604) after actuating the brush 404 in one direction 504, 506, the controller 606 controls the motor 608 to stop the brush 404, or may control the motor 206 to actuate the brush 404 in the opposing direction 504, 506 to perform a cleaning cycle (or portion of a cleaning cycle) in the opposite direction 504, 506.

When the detection surface 604 is detected, the controller 606 may stop the motor 206 to end a cleaning cycle.

The example controller 606 may be a general-purpose or an application specific processing device, such as an integrated circuit (IC), a system-on-a-chip (SoC), an integrated controller, a digital signal processor, and/or any other type of analog and/or digital circuitry. The example controller 606 may include input/output ports or interfaces, power supply circuitry, communication circuitry, volatile and/or non-volatile storage to store machine readable instructions which are executed to control the motor 206, process input from the sensor 602, and/or other aspects of the automatic emitter point cleaner 204, and/or any other ancillary circuitry.

During operation of the fan 202, the detection surface 604 may accumulate particulates, oils, and/or other contaminants that can reduce the reliability of the position sensor 602 to detect the detection surface 604. The example detection surface 604 is a smooth, electrostatically non-conductive surface that may be configured to resist adhesion by such contaminants. Additionally or alternatively, the detection surface 604 may be polished and/or have a coating which resists adhesion by contaminants. However, the detection surface 604 may nevertheless become dirty.

To improve and/or maintain detection accuracy over the life of the automatic emitter point cleaner 204, the example automatic emitter point cleaner 204 further include a detection surface cleaner 508, which cleans the detection surface 604 as the brush 404 and the detection surface 604 move with respect to the emitter frame 302. In the example of FIG. 5, the detection surface cleaner 508 is a pad (e.g., a non-abrasive material such as felt, velvet, or non-abrasive fabric) which wipes contaminants from the detection surface 604 as the detection surface 604 moves over the pad. The detection surface cleaner 508 is positioned on the emitter frame 302 along a path of the detection surface 604, such as around the detection window 502. However, the detection surface cleaner 508 may be located at other points around an inner circumference of the emitter frame 302 where the detection surface 604 can be moved over the detection surface cleaner 508.

While the detection surface 604 is located at a same circumferential position on the emitter frame 302 as the brush 404 in the illustrated examples, in other examples the detection surface 604 and the detection window 502 may be located at a different circumferential position on the emitter frame 302 than the brush 404.

While the examples of FIGS. 2-6 illustrate a two-gear implementation, other examples include three or more gears and/or a single-gear implementation in which the gear holding the emitter point brush is driven directly by a motor.

The example automatic emitter point cleaner 204 can be actuated in a single direction (e.g., clockwise or counterclockwise) and/or can be operated in both clockwise and counterclockwise to clean the ion emitters 304 in both directions.

The example automatic emitter point cleaner 204 may clean with any combination of full rotations and/or partial rotations. For example, a controller controlling the motor 206 may execute application-specific cleaning procedures including full rotations and/or partial rotations to perform particular types of cleaning.

The example automatic emitter point cleaner 204 may include position sensing to monitor the location of the emitter point brush 404. For example, the automatic emitter point cleaner 204 may determine when the brush assembly is in a default position at a start and/or finish of the cleaning process. In other examples, a controller controlling the motor 206 may track a location of the emitter point brush 404 along the inner circumference of the emitter frame 302 using a sensor (e.g., a gyroscope, a travel sensor or encoder coupled to the pinion gear 306 or the spur gear 308) and/or by tracking the speed and direction of operation of the motor 206.

Figure 8:
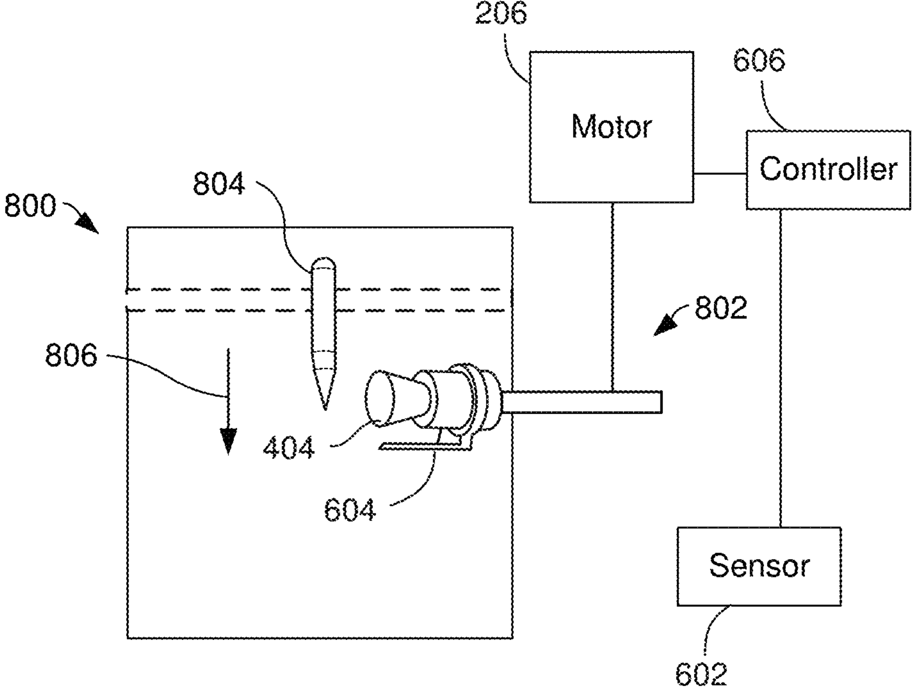
FIG. 8 is a schematic view of another example ionizer attached to an automatic emitter point cleaner, in which the emitter point is oriented in an ionization direction, in accordance with aspects of this disclosure.

FIG. 8 is a schematic view of another example ionizer 800 attached to an automatic emitter point cleaner 802, in which an ion emitter 804 is oriented along an ionization path 806. The example ion emitter 804 may be similar or identical to the ion emitters 304 of FIGS. 3-6. The example ion emitter 804 is positioned within a path for a stream of gas (e.g., the ionization path 806), which may be provided by a fan, a pressurized gas source, a pump, and/or any other source of gas.

The automatic emitter point cleaner 802 includes the brush 404 and the detection surface 604, which are coupled to an actuator such as the motor 206. For example, the brush 404 and the detection surface 604 may be attached to a gear 808 or other rotary or linear motion device, which are driven by the motor 206 to move the brush 404 into and out of contact with the emitter point 804 via rotary and/or linear motion.

The example sensor 602 is positioned to detect when the detection surface 604 is in a predetermined position, which may be within the ionization path 806 or outside of the ionization path 806. In a similar manner as discussed above, the sensor 602 provides an indication to the controller 606 as to whether the detection surface 604 is detected (e.g., when the brush 404 has completed a full movement in a rotational or linear direction. When the detection surface 604 is detected, the controller 606 may stop the motor 206 to end a cleaning cycle, or may control the motor 206 to actuate the brush 404 in an opposing direction to perform a cleaning cycle (or portion of a cleaning cycle) in the opposite direction.

As utilized herein, "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z". As utilized herein, the term "exemplary" means serving as a non-limiting example, instance, or illustration. As utilized herein, the terms "e.g.," and "for example" set off lists of one or more non-limiting examples, instances, or illustrations.

While the present method and/or system has been described with reference to certain implementations, it will be understood by those skilled in the art that various changes may be made and equivalents may be substituted without departing from the scope of the present method and/or system. In addition, many modifications may be made to adapt a particular situation or material to the teachings of the present disclosure without departing from its scope. For example, blocks and/or components of disclosed examples may be combined, divided, re-arranged, and/or otherwise modified. Therefore, it is intended that the present method and/or system not be limited to the particular implementations disclosed, but that the present method and/or system will include all implementations falling within the scope of the appended claims, both literally and under the doctrine of equivalents.

What is claimed is:

1. An automatic emitter point cleaning system, comprising:

- an emitter point configured to produce at least one of positive ions or negative ions within or proximate to an ionization delivery path;
- an emitter frame configured to hold the emitter point in or proximate to the ionization delivery path;
- a brush;
- a motor coupled to the brush to actuate the brush to move past the emitter point;
- a detection surface coupled to the brush;
- a sensor configured to detect when the brush is in a predetermined position with respect to a reference position by detecting the detection surface; and
- a detection surface cleaner configured to clean the detection surface while the brush moves with respect to the emitter frame.

2. The automatic emitter point cleaning system as defined in claim 1, further comprising a controller configured to control the motor to actuate the brush to move the brush past the emitter point.

3. The automatic emitter point cleaning system as defined in claim 2, wherein the controller is configured to control the motor to actuate the brush based on at least one of a determination by the controller or an external signal.

4. The automatic emitter point cleaning system as defined in claim 2, wherein the controller is configured to control the motor to stop the brush in response to the sensor detecting that the brush is in the predetermined position.

5. The automatic emitter point cleaning system as defined in claim 1, further comprising a plurality of emitter points in a same axial plane as the emitter point and the brush, the emitter frame configured to hold the plurality of emitter points radially inward from the emitter frame and into the ionization path, the motor configured to move the brush into contact with each of the plurality of emitter points.

6. The automatic emitter point cleaning system as defined in claim 5, wherein the plurality of emitter points are arranged in a substantially circular or polygonal arrangement.

7. The automatic emitter point cleaning system as defined in claim 6, further comprising:

- a first gear coupled to the brush, configured to hold the brush in a same axial plane as the emitter point, and configured to move the brush into contact with the emitter point; and
- a second gear coupled between the motor and the first gear to actuate the first gear in response to actuation by the motor, wherein the plurality of emitter points are arranged around or adjacent to an inner circumference of the first gear.

8. The automatic emitter point cleaning system as defined in claim 6, wherein the substantially circular or polygonal arrangement is substantially coaxial with a fan.

9. The automatic emitter point cleaning system as defined in claim 1, wherein the motor is a bidirectional motor configured to move the brush in either direction.

10. The automatic emitter point cleaning system as defined in claim 1, wherein the detection surface cleaner is positioned on the emitter frame adjacent the predetermined position.

11. The automatic emitter point cleaning system as defined in claim 1, wherein the detection surface cleaner comprises a pad configured to wipe contaminants from the detection surface as the detection surface moves over the pad.

12. The automatic emitter point cleaning system as defined in claim 11, wherein the pad is a non-abrasive material.

13. The automatic emitter point cleaning system as defined in claim 1, wherein the detection surface cleaner is positioned on the emitter frame along a path of the detection surface.

14. The automatic emitter point cleaning system as defined in claim 1, wherein the emitter point is configured to generate ionization.

15. The automatic emitter point cleaning system as defined in claim 1, further comprising:

- a first gear coupled to the brush, configured to hold the brush in a same axial plane as the emitter point, and configured to move the brush into contact with the emitter point; and
- a second gear coupled between the motor and the first gear to actuate the first gear in response to actuation by the motor.

16. The automatic emitter point cleaning system as defined in claim 1, wherein the detection surface comprises a smooth, electrostatically non-conductive surface configured to resist adhesion by contaminants.

17. The automatic emitter point cleaning system as defined in claim 16, wherein the detection surface is a polished surface.

18. The automatic emitter point cleaning system as defined in claim 16, wherein the detection surface comprises a coating configured to resist adhesion by contaminants.

19. The automatic emitter point cleaning system as defined in claim 1, further comprising a fan configured to direct a stream of gas along the ionization path.

20. The automatic emitter point cleaning system as defined in claim 19, wherein the emitter point is oriented in a same direction as the ionization path.

* * * * *